US00PP30600P2

(12) United States Plant Patent
Bentley

(10) Patent No.: US PP30,600 P2
(45) Date of Patent: Jun. 25, 2019

(54) ***ARMERIA* PLANT NAMED 'DREAM WEAVER'**

(50) Latin Name: *Armeria pseudarmeria*
Varietal Denomination: Dream Weaver

(71) Applicant: Plant Growers Australia Pty Ltd, Wonga Park (AU)

(72) Inventor: Howard Bentley, Lilydale (AU)

(73) Assignee: Plant Growers Australia Pty Ltd, Wonga Park (AU)

( * ) Notice: Subject to any disclaimer, the term of this patent is extended or adjusted under 35 U.S.C. 154(b) by 0 days.

(21) Appl. No.: 15/998,275

(22) Filed: Jul. 27, 2018

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Armeria* plant named 'Dream Weaver', characterized by its deep rose-pink colored flowers, dark green-colored foliage, and moderately vigorous, compact-mounded growth habit, is disclosed.

1 Drawing Sheet

Latin name of genus and species of plant claimed: *Armeria pseudarmeria.*

Variety denomination: 'Dream Weaver'.

BACKGROUND OF THE INVENTION

The present invention relates to a new and distinct cultivar of *Armeria* plant botanically known as *Armeria pseudarmeria* and hereinafter referred to by the cultivar name 'Dream Weaver'.

The new cultivar originated in a controlled breeding program in Wonga Park, Australia during October 2011. The objective of the breeding program was the development of *Armeria* cultivars that have an extended flowering season, shorter scapes and a compact-mounded habit.

The new interspecific *Armeria* cultivar is the result of cross-pollination. The female (seed) parent of the new cultivar is *Armeria* 'Sweet Dreams', U.S. Plant Pat. No. 29,612, characterized by its light purple-colored flowers, dark green-colored foliage, and moderately vigorous, compact-mounded growth habit. The male (pollen) parent of the new cultivar is a proprietary *Armeria pseudarmeria* breeding selection, coded IB010-3, not patented, characterized by its medium purple-colored flowers, medium green-colored foliage, and moderately vigorous, mounded growth habit. The new cultivar was discovered and selected as a single flowering plant within the progeny of the above stated cross-pollination during February 2013 in a controlled environment in Wonga Park, Australia.

Asexual reproduction of the new cultivar by division since February 2013 in Wonga Park, Australia and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Dream Weaver' as a new and distinct cultivar of *Armeria* plant:

1. Deep rose-pink colored flowers;
2. Dark green-colored foliage; and
3. Moderately vigorous, compact-mounded growth habit.

Plants of the new cultivar differ from plants of the female parent primarily in having a darker flower color. Plants of the new cultivar differ from plants of the male parent primarily in having shorter scapes and a longer flowering season.

Of the many commercially available *Armeria* cultivars, the most similar in comparison to the new cultivar is 'Daydream', U.S. Plant Pat. No. 29,831. However, in comparison, plants of the new cultivar differ from plants of 'Daydream' in at least the following characteristics:

1. Plants of the new cultivar have a darker flower color than plants of 'Daydream';
2. Plants of the new cultivar have shorter scapes than plants of 'Daydream'; and
3. Plants of the new cultivar have smaller corollas, as measured by length and width, than plants of 'Daydream'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Dream Weaver'. The plants were approximately five and a half months old and grown in one-gallon containers for approximately two months in a glass covered greenhouse and then grown for approximately six weeks in a garden bed in West Chicago, Ill.

DETAILED BOTANICAL DESCRIPTION

Figure 1:
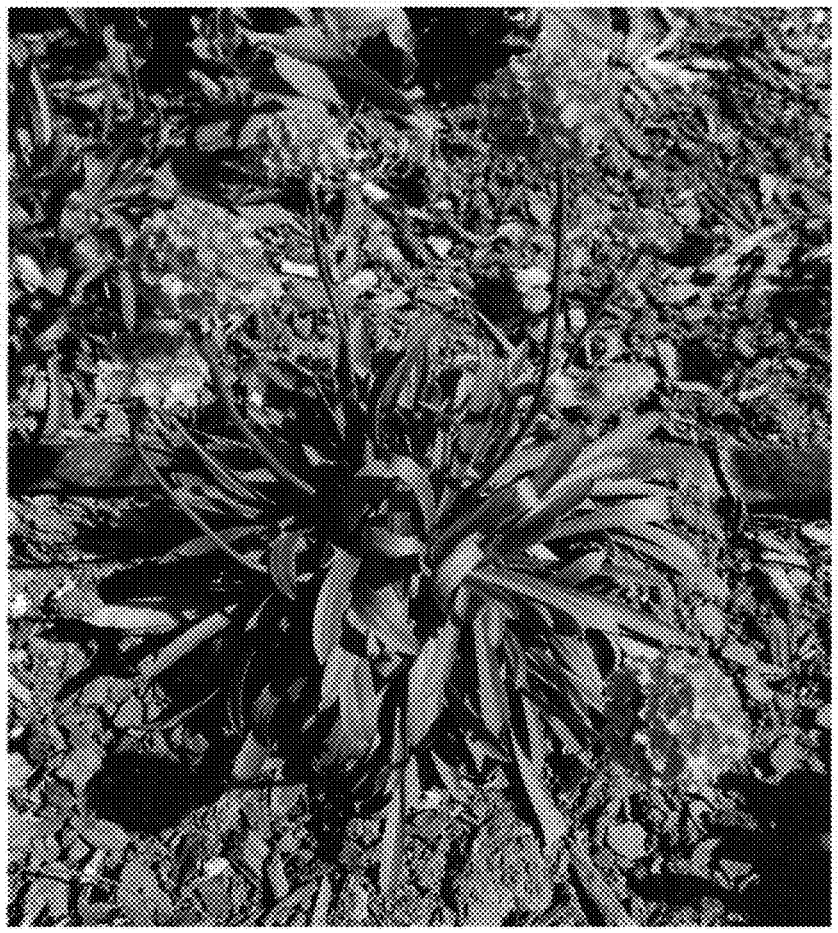
FIG. 1 illustrates a side view of the overall growth and flowering habit of 'Dream Weaver'.
Figure 2:
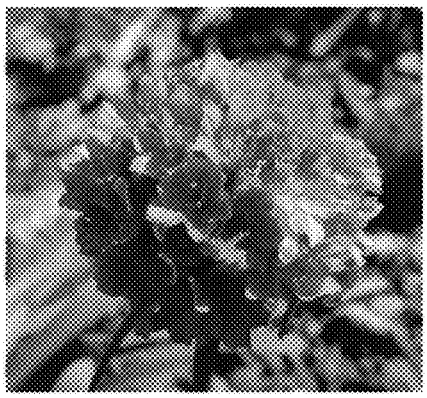
FIG. 2 illustrates a close-up view of an individual inflorescence of 'Dream Weaver'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe five and a half month old plants produced from cuttings from stock plants and grown in a glass-covered greenhouse under conditions comparable to those used in commercial practice. The plants were grown utilizing a soilless growth medium in one-gallon containers for approximately two months in Elburn, Ill. before transplant into a garden bed in West Chicago, Ill. and grown for approximately six weeks. Greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Armeria pseudarmeria* 'Dream Weaver'.

Parentage:

*Female parent.*—'Sweet Dreams', U.S. Plant Pat. No. 29,612.

*Male parent.*—Proprietary *Armeria pseudarmeria* breeding selection, coded IB010-3, not patented.

Propagation:

*Type cutting.*—Terminal.

*Time to initiate roots.*—Approximately 15 to 18 days.

*Time to produce a rooted cutting.*—Approximately 6 to 7 weeks.

*Root description.*—Fine, fibrous.

*Rooting habit.*—Freely branching.

Plant description:

*Commercial crop time.*—Approximately 14 to 16 weeks from a rooted cutting to finish in a 15 cm pot, vernalization not required for flowering.

*Growth habit and general appearance.*—Herbaceous perennial, moderately vigorous, compact-mounded.

*Hardiness.*—USDA Zone 6a (−10° F. to −5° F./−23.3° C. to −20.6° C.).

*Size.*—Height from soil level to top of plant plane: Approximately 21.0 cm. Height from soil level to top of foliage: Approximately 10.0 cm. Width: Approximately 21.5 cm.

*Branching habit.*—Clump forming. Quantity of main clumps per plant: Approximately 9.

Foliage description:

*General description.*—Quantity of leaves per main clump: Approximately 11. Fragrance: None detected. Form: Simple. Arrangement: Basal rosette.

*Leaves.*—Shape: Oblanceolate. Margin: Entire. Apex: Acute. Base: Attenuate, sessile. Venation pattern: Parallel. Length of mature leaf: Approximately 9.0 cm. Width of mature leaf: Approximately 1.0 cm. Texture of upper and lower surfaces: Glabrous. Color of upper surface of young foliage: 137B with base of NN155D, slightly glaucous, venation indistinguishable from laminae. Color of lower surface of young and mature foliage: 137C with base of NN155D, slightly glaucous, venation indistinguishable from laminae. Color of upper surface of mature foliage: 137A with base of NN155D, slightly glaucous, venation indistinguishable from laminae.

Flowering description:

*Flowering habit.*—'Dream Weaver' is freely flowering under outdoor growing conditions with substantially continuous blooming from spring through autumn.

*Lastingness of inflorescence on the plant.*—Color holds for approximately 2 weeks.

Inflorescence description:

*General description.*—Type: Head, globose, terminal on scape, facing upright. Quantity per plant: Approximately 6. Fragrance: None detected. Length or height: Approximately 1.7 cm. Width: Approximately 2.6 cm. Quantity of fully open flowers per inflorescence: Approximately 40.

*Scape.*—Strength: Strong. Aspect: Erect. Length: Approximately 16.0 cm. Diameter: Approximately 2.5 mm. Texture: Glabrous, slightly glaucous. Color: 137B maturing to NN137A. Involucral sheath length: Approximately 9.0 mm.

*Involucral bracts.*—Quantity: 16, in multiple whorls. Aspect: Cupped to flat, pointing downward when inflorescence fully open. Shape: Lanceolate to oblong. Margin: Entire. Apex: Acute. Base: Truncate. Length of outermost: Approximately 1.7 cm. Width of outermost: Approximately 5.0 mm. Length of innermost: Approximately 8.0 mm. Width of innermost: Approximately 4.0 mm. Texture of upper (inner) surface: Glabrous. Texture of lower (outer) surface: Glabrous. Color of upper (inner) surface: 137B with 145B at base and transparent, colorless margins. Color of lower (outer) surface: 137A with 145A at base and transparent, colorless margins.

Flower description:

*Type.*—Salverform, in clusters of four.

*Bud.*—Rate of opening: Generally takes 5 to 6 days for bud to progress from first color to fully open flower.

*Bud just before opening.*—Shape: Tubular. Length: Approximately 7.0 mm. Width: Approximately 2.0 mm. Color: Sepal centers of 145C with transparent, colorless margins; petals of N78A.

*Corolla.*—Length: Approximately 1.0 cm. Width: Approximately 1.1 cm.

*Petals.*—Quantity: 5. Shape: Obovate. Margin: Entire. Apex: Emarginate to obtuse. Base: Attenuate. Length: Approximately 9.0 mm. Width: Approximately 4.0 mm. Color of upper surface when first open: Closest to NN78A with base of NN155D. Color of lower surface when first open: Closest to NN78B with base of NN155D. Color of upper surface when fully open: Closest to NN78B to NN78C with base of NN155D. Color of lower surface when fully open: Closest to NN78C to NN78D with base of NN155D.

*Calyx.*—Shape: Cupped. Diameter: Approximately 3.0 mm.

*Sepals.*—Quantity per flower: 5, fused sides and base to form a tube. Shape: Obovate. Margin (unfused portion): Entire, wavy. Apex: Aristate. Length: Approximately 6.0 mm. Width: Approximately 1.5 mm. Texture of inner surface: Glabrous. Texture of outer surface: Sparsely pubescent. Color of inner and outer surfaces: Centers of 145A and 145C with transparent, colorless margins.

*Pedicel.*—Strength: Strong, flexible. Length: Approximately 2.0 mm. Diameter: Less than 1.0 mm. Texture: Glabrous. Color: 145D.

*Reproductive organs.*—Androecium: Stamen quantity: 5 per flower. Stamen length: Approximately 6.0 mm. Filament color: NN155D. Anther shape: Oblong, dorsifixed. Anther length: Approximately 1.0 mm. Anther color: 154C. Pollen amount: Sparse. Pollen color: 2C. Gynoecium: Pistil quantity: 1 per flower, with 5 distinct styles. Pistil length: Approximately 6.0 mm. Stigma shape: Pointed. Stigma color: NN155D. Style length: Approximately 5.0 mm. Style color: NN155D. Style texture: Glabrous with feather-like pubescence located in lower third. Ovary diameter: Approximately 1.0 mm. Ovary color: Closest to 145A.

Seed and fruit production: Neither seed nor fruit production has been observed.

Disease and pest resistance: Resistance to pathogens and pests common to *Armeria* has not been observed.

What is claimed is:

1. A new and distinct cultivar of *Armeria* plant named 'Dream Weaver', substantially as herein illustrated and described.

* * * * *